(12) United States Patent
Molina et al.

(10) Patent No.: US 10,185,051 B2
(45) Date of Patent: Jan. 22, 2019

(54) VARIABLE DAMPING CONTROL FOR NUCLEAR MAGNETIC RESONANCE DATA ACQUISITION SYSTEM TO ENHANCE OILFIELD LOGGING PERFORMANCE

(71) Applicant: Schlumberger Technology Corporation, Sugar Land, TX (US)

(72) Inventors: Diogenes David Molina, Sugar Land, TX (US); Eugene Janssen, Sugar Land, TX (US); Krishnamurthy Ganesan, Sugar Land, TX (US); Nicholas Heaton, Sugar Land, TX (US); Vassilis Varveropoulos, Katy, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 260 days.

(21) Appl. No.: 15/143,267

(22) Filed: Apr. 29, 2016

(65) Prior Publication Data

US 2017/0315258 A1    Nov. 2, 2017

(51) Int. Cl.
*G01R 33/58* (2006.01)
*G01V 3/32* (2006.01)
*G01R 33/44* (2006.01)
*G01N 15/08* (2006.01)

(52) U.S. Cl.
CPC ............... *G01V 3/32* (2013.01); *G01R 33/58* (2013.01); *G01N 15/08* (2013.01); *G01N 2015/0846* (2013.01); *G01R 33/448* (2013.01)

(58) Field of Classification Search
CPC .... G01N 24/08; G01N 24/081; G01N 24/082; G01N 24/084; G01N 24/10; G01R 33/3808; G01R 33/445; G01R 33/448; G01V 3/14; G01V 3/32
See application file for complete search history.

(56) References Cited

U.S. PATENT DOCUMENTS

| | | | |
|---|---|---|---|
| 5,051,700 A | 9/1991 | Fox | |
| 6,255,817 B1 * | 7/2001 | Poitzsch | G01N 24/081 324/300 |
| 2002/0153136 A1 * | 10/2002 | Kruspe | G01V 3/32 166/250.01 |

OTHER PUBLICATIONS

Hoult, D. I., "Fast Recovery, High Sensitivity NMR Probe and Preamplifier for Low Frequencies," Review of Scientific Instrumentation, 1979, 50(2), pp. 193-200.
Baudin, E. et al., "An Active Feedback Scheme for Low Field NMR Experiments," Journal of Physics: Conference Series, 2011, 294(1), 8 pages.

* cited by examiner

*Primary Examiner* — Tung X Nguyen (57) ABSTRACT

A method to calibrate a nuclear magnetic resonance tool is disclosed having steps of starting a nuclear magnetic resonance sequence from the nuclear magnetic resonance tool, disabling an active damping circuit in the nuclear magnetic resonance tool, collecting auxiliary calibration data for the nuclear magnetic resonance tool, estimating a natural Q value for the nuclear magnetic resonance tool, determining an optimal active damping setting for the tool, deploying the optimal active damping setting for the tool, collecting nuclear magnetic resonance response data generated from the nuclear magnetic resonance sequence and calibrating the nuclear magnetic resonance data.

12 Claims, 8 Drawing Sheets

VARIABLE DAMPING CONTROL FOR NUCLEAR MAGNETIC RESONANCE DATA ACQUISITION SYSTEM TO ENHANCE OILFIELD LOGGING PERFORMANCE

CROSS-REFERENCE TO RELATED APPLICATIONS

None.

FIELD OF THE INVENTION

Aspects of the description relate to nuclear magnetic resonance well logging tools. More specifically, aspects relate to providing an arrangement in a nuclear magnetic resonance well logging tool that provides for a variable active damping control mechanism.

BACKGROUND INFORMATION

Nuclear magnetic resonance (NMR) well logging tools measure the properties of nuclear spins in the formation such as the signal amplitude, longitudinal (or spin-lattice) relaxation time ($T_1$), and transverse (or spin-spin) relaxation time ($T_2$). Information on these NMR properties aids in the determination of basic formation properties such as permeability and porosity, as well as fluid properties such as fluid type.

Measurements of formation properties are achieved by applying a series of pulses followed by or interleaved with data acquisition. Each particular measurement configuration is called a pulse sequence. For example, transverse relaxation time, $T_2$, is often measured with the Curr-Purcell-Meiboom-Gill (CPMG) pulse sequence or other variants, in which trains of spin echoes are generated by a series of pulses. In another example, longitudinal relaxation time, $T_1$, may be measured by applying a series of pulse sequences with variable wait time in between to encode the longitudinal recovery in spin echo amplitudes. In another example, transverse relaxation time, $T_2$ measurement and longitudinal relaxation time $T_1$ measurement are combined together to obtain two-dimensional information on formation fluids. In general, any nuclear magnetic resonance measurements including but not limited to the above examples may be combined to obtain multi-dimensional information on the formation or formation fluids.

Once the nuclear magnetic resonance data are acquired, a mathematical inversion process is applied to produce the distribution of measured properties that reflects the anisotropy of formation or formation fluids. For example, $T_2$ distribution represents the distribution of pore sizes within the formation, and the area under the $T_2$ curve is the porosity filled with formation fluids. Interpretation of pore size distribution and logarithmic mean $T_2$ are used to calculate petrophysical parameters such as permeability and the amount of free/bound fluid.

The pulse sequence used during logging is usually determined by the measured property. In logging oilfields, the $T_1$ and $T_2$ properties encountered may range from a fraction of a millisecond to several seconds. The time-separation between pulses in a pulse sequence is known as the echo spacing (TE). TE must be lower than the lowest $T_2$ to be measured in the formation, consequently, to measure formation properties with $T_2$ on the order of fractions of milliseconds, the pulse sequence itself must contain pulse trains with TE in the order of fractions of milliseconds or lower.

The characteristics of NMR oilfield logging equipment limit the minimum echo spacing, TE, to values that can be achieved. This in turn limits the minimum value of $T_2$ that can be measured and can prevent more in-depth understanding of the properties of a given hydrocarbon reservoir, consequently, it is desirable to devise new mechanisms to reduce the minimum echo spacing that NMR logging tools can achieve.

The inherent nature of oilfield logging makes it so that the environmental conditions under which the logging equipment operates change over time as the device traverses through different layers of the formation. It is known that the electrical response of the logging equipment can be affected by some of those environmental conditions. This can lead to performance degradation, and often imposes the need for post-processing of the logged data to compensate for those variations. It is desirable to implement mechanisms to compensate for formation variability in an automated fashion. These mechanisms could allow for measurement compensation and performance optimization in real-time as the formation is being logged, and preclude the need for data post-processing.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one non-limiting embodiment, a method for processing nuclear magnetic resonance data is disclosed wherein a nuclear magnetic resonance tool is placed in a wellbore, the nuclear magnetic resonance tool is activated to generate a signal to a geological formation, followed by active damping the nuclear magnetic resonance tool and receiving a response signal from the geological formation.

In another non-limiting embodiment, a method to calibrate a nuclear magnetic resonance tool is disclosed wherein actions of starting a nuclear magnetic resonance sequence from the nuclear magnetic resonance tool, disabling an active damping circuit in the nuclear magnetic resonance tool, collecting auxiliary calibration data for the nuclear magnetic resonance tool, estimating a natural Q value for the nuclear magnetic resonance tool, determining an optimal active damping setting for the tool, deploying the optimal active damping setting for the tool, collecting nuclear magnetic resonance response data generated from the nuclear magnetic resonance sequence and calibrating the nuclear magnetic resonance data are performed.

In another non-limiting embodiment, a method for processing nuclear magnetic resonance data is disclosed having steps of placing a nuclear magnetic resonance tool in a wellbore, starting a nuclear magnetic resonance sequence from the nuclear magnetic resonance tool, disabling an active damping circuit in the nuclear magnetic resonance tool, collecting auxiliary calibration data for the nuclear magnetic resonance tool, estimating a natural Q value for the nuclear magnetic resonance tool, determining an optimal active damping setting for the tool, performing a multi-dimensional master calibration master calibration based on the natural system Q and a variable active damping setting, deploying the optimal active damping setting for the tool, collecting nuclear magnetic resonance response data generated from the nuclear magnetic resonance sequence and calibrating the nuclear magnetic resonance data based upon the Q value.

BRIEF DESCRIPTION OF THE DRAWINGS

In the drawings, sizes, shapes, and relative positions of elements are not drawn to scale. For example, the shapes of various elements and angles are not drawn to scale, and some of these elements may have been arbitrarily enlarged and positioned to improve drawing legibility.

DETAILED DESCRIPTION

Figure 1:
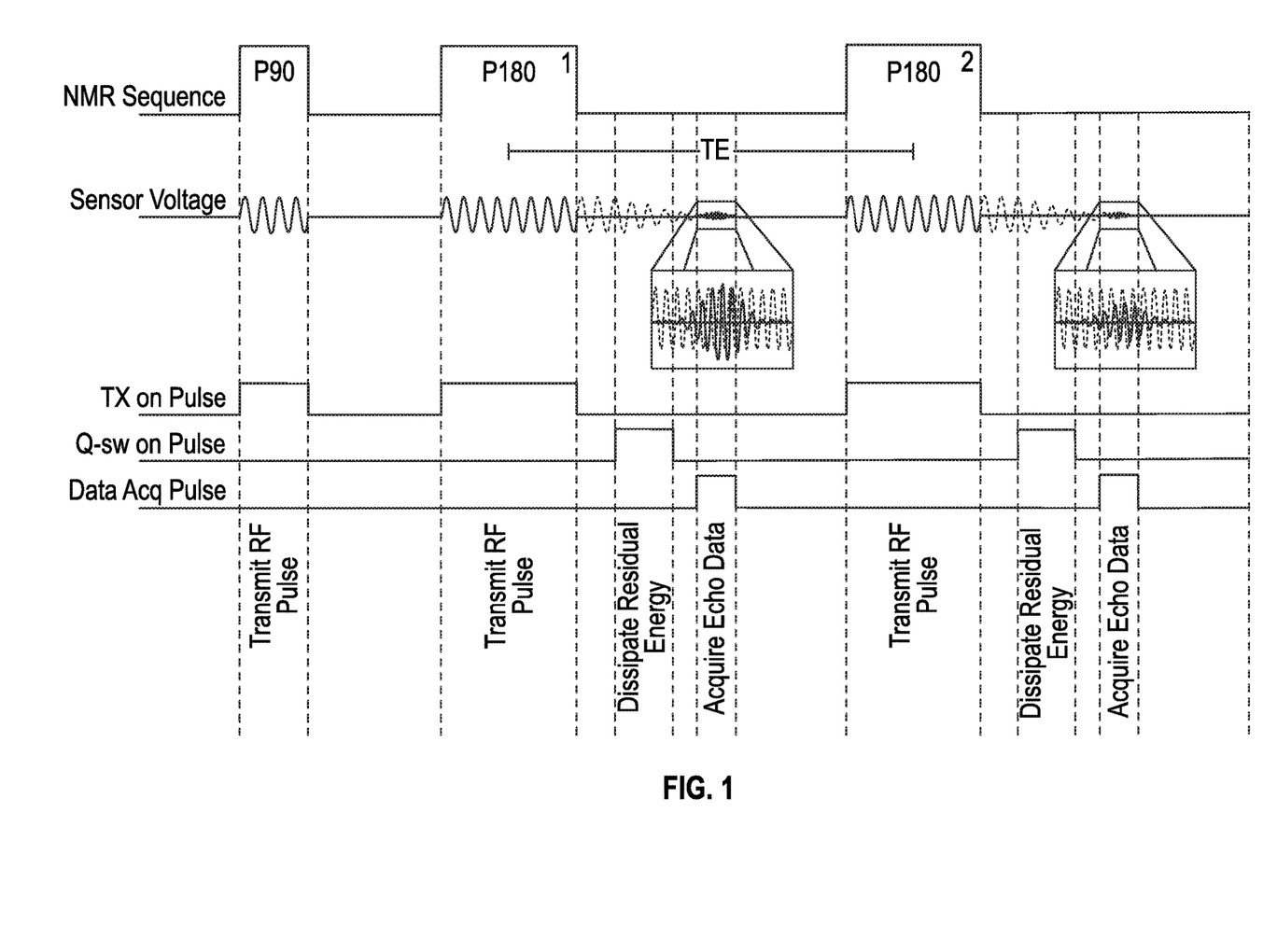
FIG. 1 is a diagrammatic representation of a nuclear magnetic resonance simplified sequence.

The main events in a generic NMR pulse sequence are illustrated in FIG. 1. During the TX ON pulse, a transmitter applies a sinusoidal voltage to the antenna at a specified frequency and phase. From this voltage, the antenna generates a resonant frequency pulse towards the formation being logged. After transmission stops, the formation will generate a very small response known as an "echo" and illustrated in red in FIG. 1. Unfortunately, this echo response is typically small (around 1 microvolt) such that a receiver must amplify the response significantly to improve the signal and so the echo can be sampled into the tool's digital signal processing chain without significant quantization error. Any noise or distortion received will also be amplified, so it is necessary that no additional noise is added by the receiver circuitry.

After transmission, the capacitive and inductive elements in the antenna contain significant amounts of residual energy. Due to low natural damping in the antenna, this energy is dissipated very slowly and there may be substantial residual "ringing" as shown in blue in FIG. 1. The bulk of this residual energy can be dissipated quickly by introducing high resistive damping into the circuit using a device commonly known as a Q-switch; however, this Q-switch has to be disabled (turned-off) before the echo arrives, otherwise the echo signal is also dissipated and the formation response is lost. The Q-switch turn-off transient is known to cause the circuit to "ring anew". In practice, this ringing can be large enough to corrupt the echo signal to the point of making it unusable unless something is done to mitigate it. One of the best methods to do so is through an active damping circuit. Active damping circuits introduce additional damping, causing the ringing injection from the Q-switch turn-off to decay faster, without adding significant noise.

Figure 2:
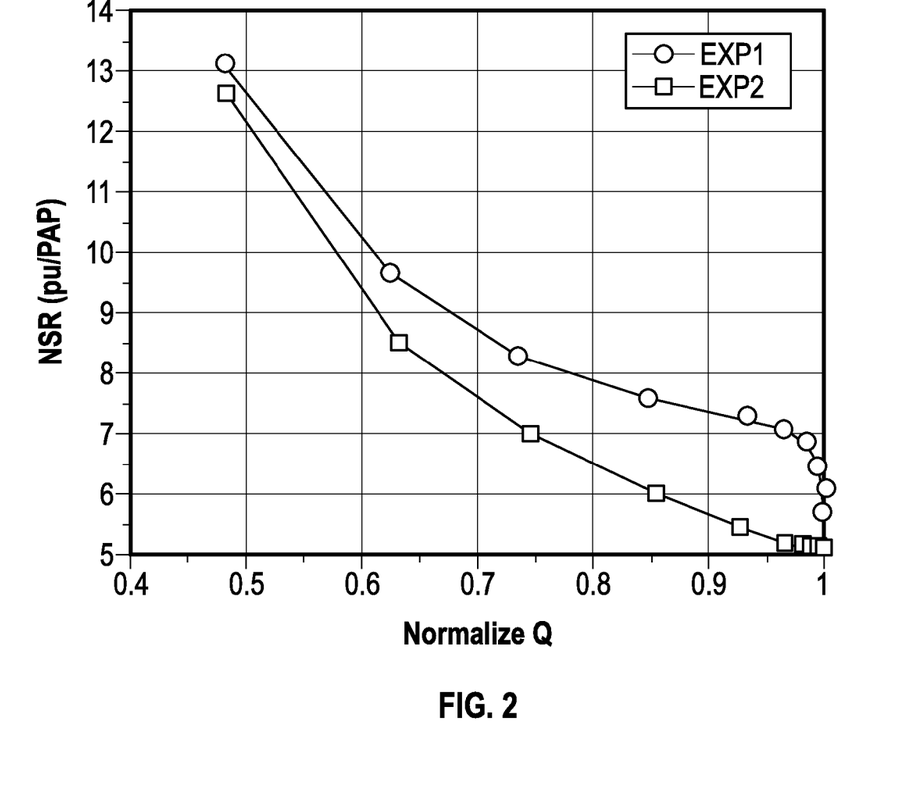
FIG. 2 is a change in noise to signal ratio with Q-Q variations that arise from sample salinity.
Figure 3:
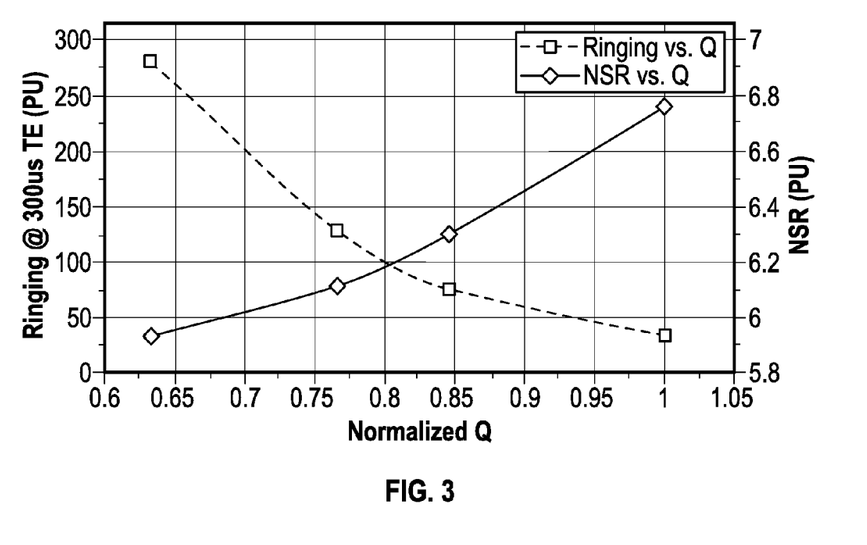
FIG. 3 is a change in noise to signal ratio and ringing with Q-Q variations that are due to circuit parameter changes.

Experimental data such as that illustrated in FIG. 2 and FIG. 3 indicates that there is a strong correlation between the overall tool noise, represented as the noise to signal ratio (NSR) performance metric in the figures, and the amount of damping in the system, represented as the quality factor (Q) in the figures. Note there is an inverse relation between Q and damping (high Q→low damping, low Q→high damping). As Q increases, either due to changes in the sample's salinity or due to changes in the electronic circuit, the noise to signal ratio decreases. Also, as Q decreases, the noise to signal ratio increases. As one would expect, the opposite is true for the ringing performance metric as shown in FIG. 3. As illustrated in FIG. 2, different salinity earth formations may be evaluated, providing a significant benefit to evaluators. The methods and apparatus described, therefore, can be modified, as described herein to adapt to environmental conditions, therefore the configurations disclosed should not be considered limiting.

The following facts are worth noting:
1—The salinity of the sample and the resulting Q cannot be controlled and will change depending on logging conditions.
2—Low noise to signal ratio and low ringing are desired for all conditions, so the optimization of the tool's electronics results in a tradeoff between ringing and noise to signal ratio.
3—The weight of importance between ringing and noise to signal ratio depends on the configuration of the measurement being made. For measurements with long echo spacings, ringing is less important than noise to signal ratio. For measurements with short echo spacings, ringing is more important than noise to signal ratio.
4—The parameters for the electronics are fixed and optimized for a "nominal" logging condition and measurement configuration. Once the condition or configuration changes, the tuning is no longer optimal and the performance of the measurement degrades.

The amount of damping introduced by the active damping circuit is determined by the electrical parameters of the circuit. In non-limiting embodiments, the aspects disclosed make those parameters variable and controllable. By doing so, the resulting system Q can be manipulated in real-time to adjust for the logging conditions or the measurement configuration. The added capabilities allow for:
1—Compensating for the effect of salinity such that the system Q remains constant regardless of logging conditions.
2—Pursuing the optimal compromise between ringing and noise to signal ratio based on the measurement being made. For low echo spacing, TE measurements, the system Q is intentionally lowered. For high echo spacing, TE measurements, the system Q is intentionally increased.

Figure 4:
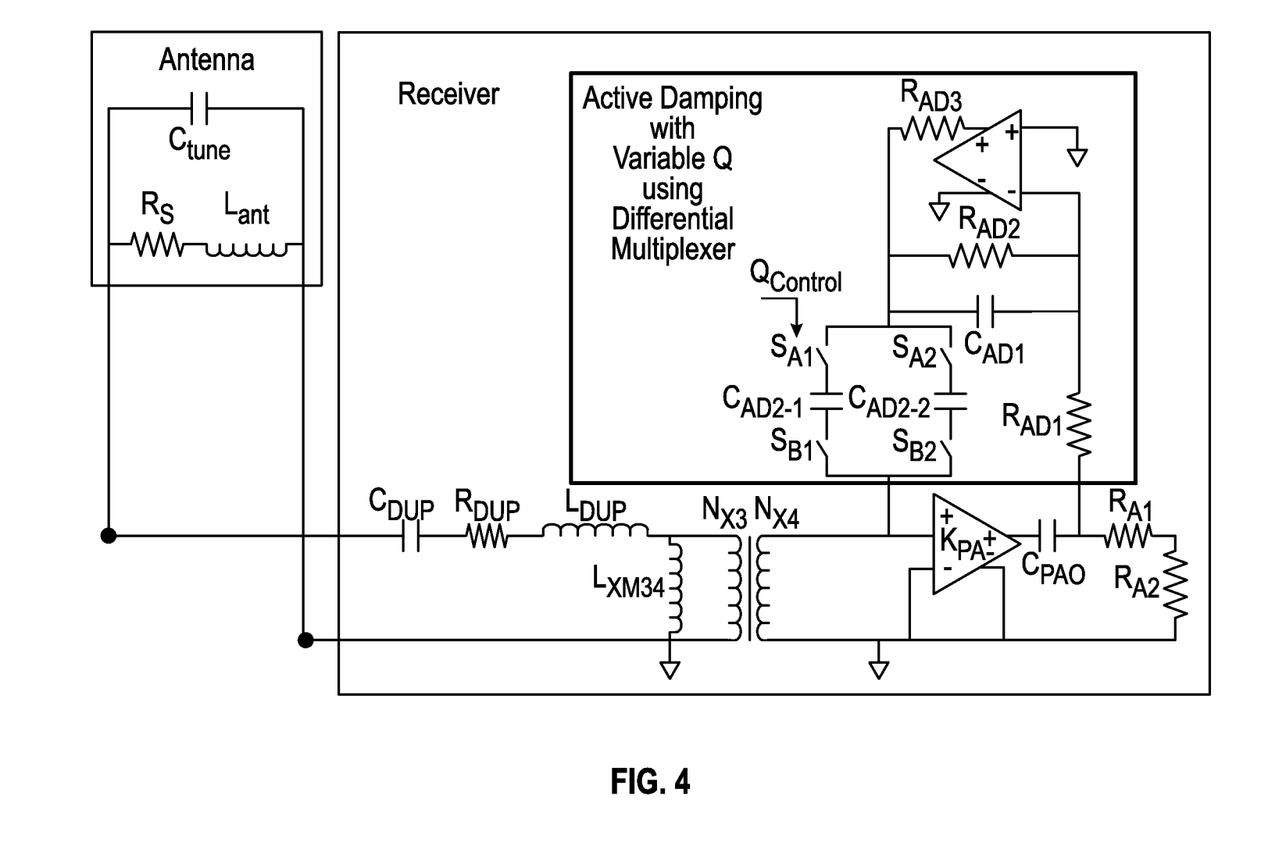
FIG. 4 is an example embodiment of a non-limiting configuration used for variable damping control of nuclear magnetic resonance data.
Figure 5:
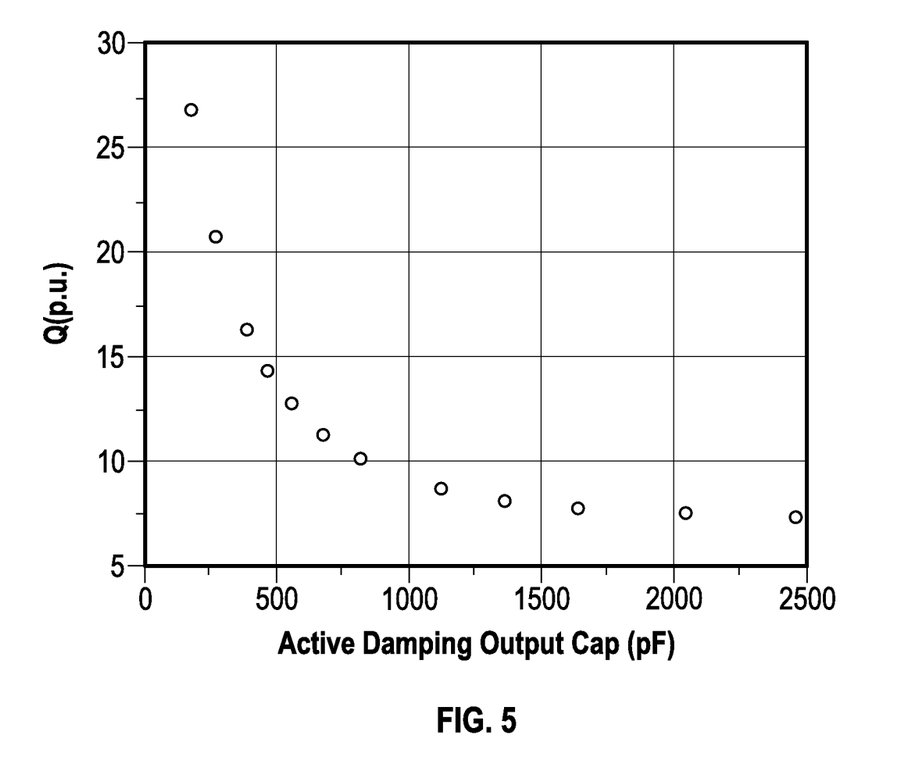
FIG. 5 is a graph of the effect of changes in the value of capacitance at the output of the active damper on the system.
Figure 6:
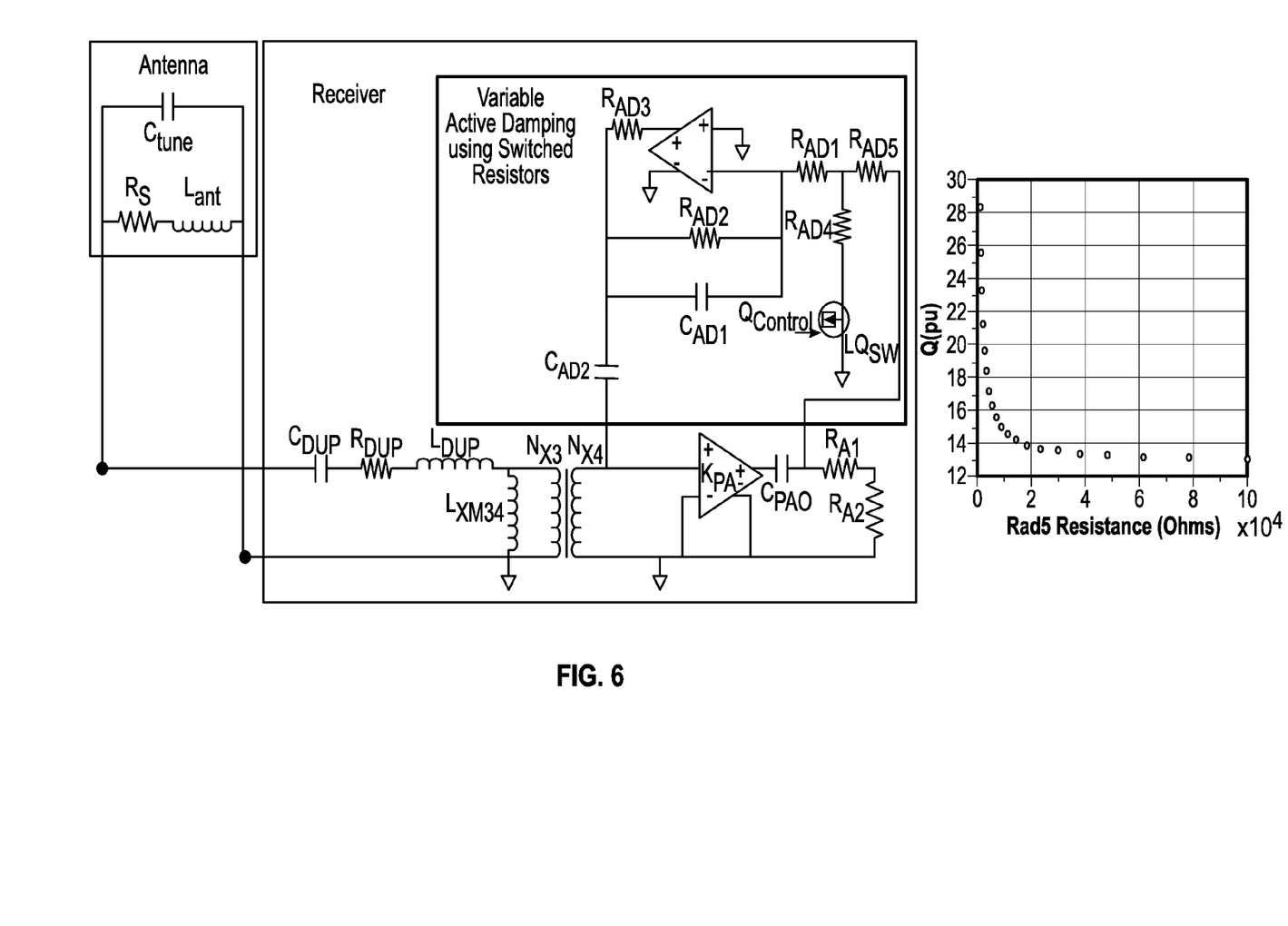
FIG. 6 is a second example embodiment of a non-limiting configuration used for variable damping control of nuclear magnetic resonance data.
Figure 7:
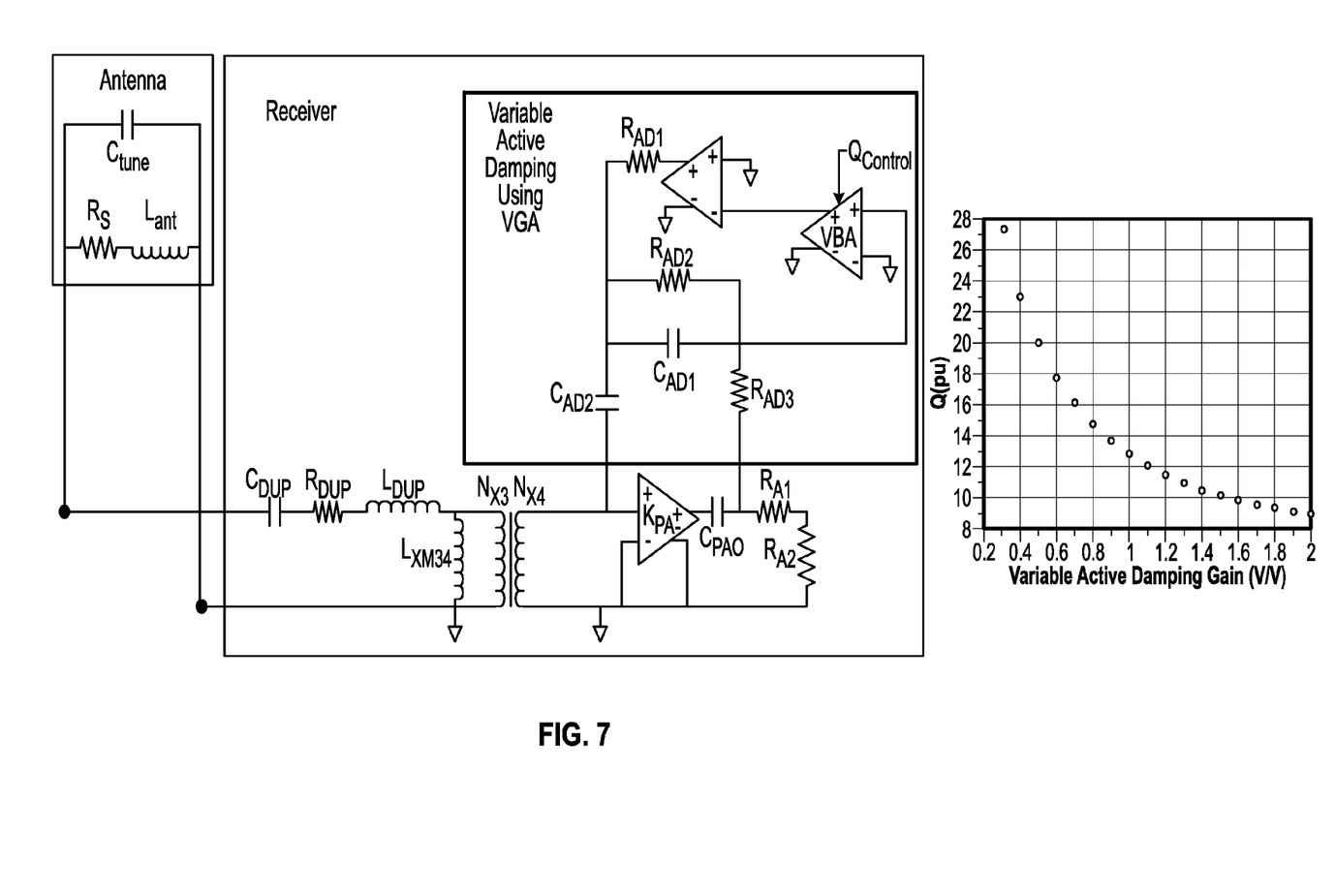
FIG. 7 is a third example embodiment of a non-limiting configuration used for variable damping control of nuclear magnetic resonance data.

A simplified view of one example embodiment is illustrated in FIG. 4. The parameter being varied is the output capacitance of an active damping circuit using a differential multiplexer. The signal controlling the multiplexer is produced by an external digital control system. This digital control system has the appropriate information regarding the logging conditions and measurement configuration to select the optimal Q at any given time. Referring to FIG. 5, the effects of changes in the value of capacitance at the output of the active damper on the system Q is illustrated. The value of Q is graphed along an "x" axis of active damping output capacitance in pF. Referring to FIG. 6, the left side of the FIGS. shows a variable active damping circuit using switched resistors. The configuration illustrated in FIG. 6 uses switched resistors, as compared to FIG. 4 which uses a differential multiplexer. The right side of FIG. 6 illustrates the effects that the system of FIG. 6 has on different values. The value of Q is graphed versus resistance in ohms. As evident from the data, the value of Q rapidly decreases up to a value of resistance of 1 ohm and then gradually decreases thereafter. Referring to FIG. 7 left side, this configuration uses a variable gate array arrangement for variable active damping as another non-limiting embodiment. This configuration may be used as an alternative to FIG. 4 and FIG. 6. The right side of FIG. 7 shows the effect on values such as Q and variable active damping over a range of values. As Q decreases, the variable active damping gain decreases as illustrated.

Figure 8:
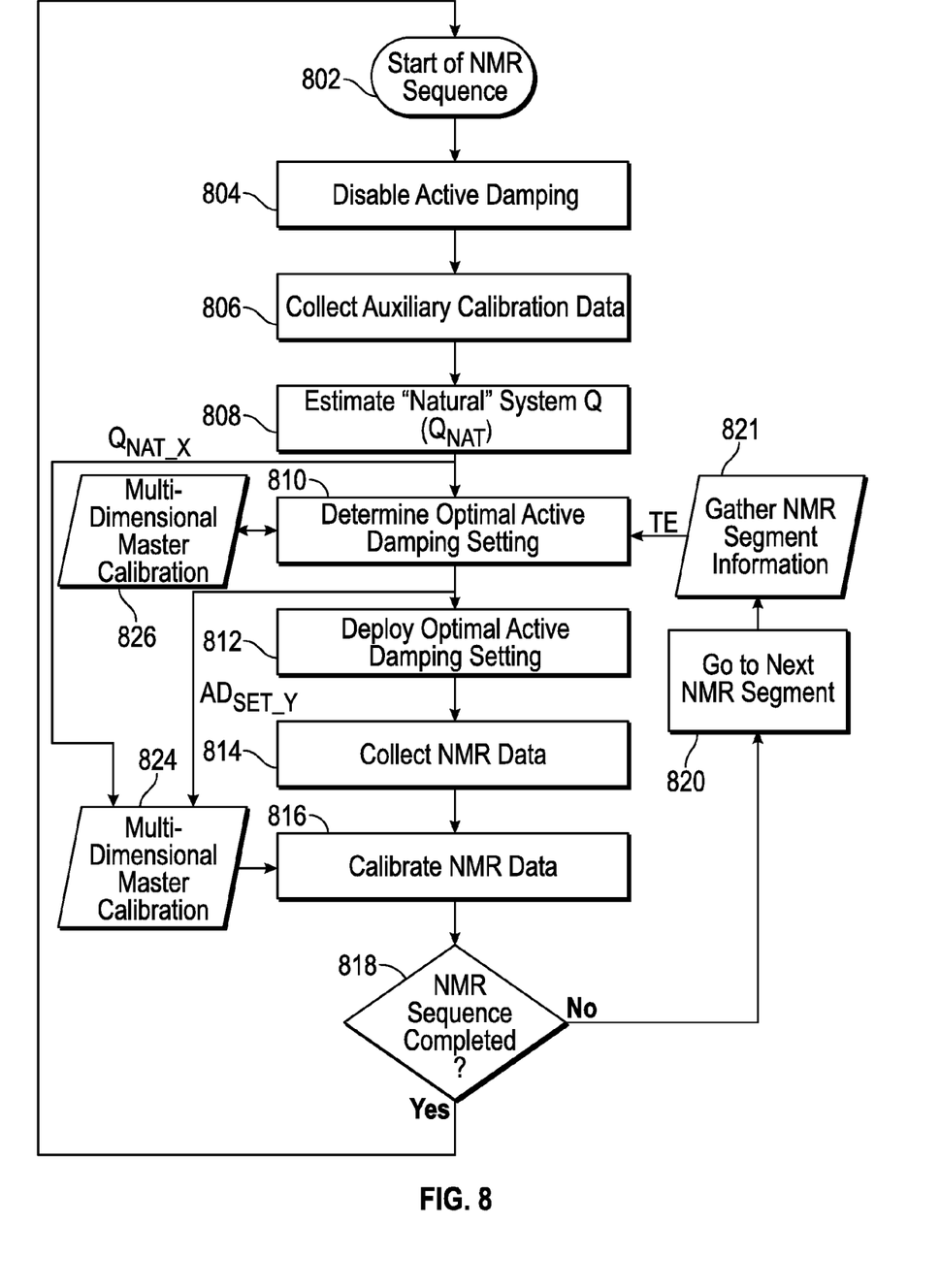
FIG. 8 is a method for selection of an optimal Q value.

The control system to select the optimal hardware setting follows the steps illustrated in FIG. 8. First, the active damper is disabled to avoid any interference with the auxiliary calibration measurement. The auxiliary calibration measurement is taken to determine the logging condition. This condition is characterized by the natural Q (QNAT). The echo spacing (TE) of the measurement about to be made is collected as well. Once QNAT and TE are known, it is possible to use calibration data collected a-priory to select the variable active damping setting that achieves the optimal compromise between noise and ringing. This setting is then implemented and the NMR measurement made. The calibration data is again used to calibrate the measurement, allowing the elimination of unwanted variability in the products caused by the variable active damping circuit.

A comprehensive master-calibration database is needed for proper control of the variable active damping circuit. The first dataset in the database captures the effect of the variable active damping setting to the system Q for a given set of logging conditions.

TABLE 1

System Q With Respect to Logging Conditions and Variable Active Damping Setting

| | | Natural System Q | | |
|---|---|---|---|---|
| | | $Q_{NAT\_1}$ | $Q_{NAT\_2}$ | ... $Q_{NAT\_N}$ |
| Variable Active Damping Setting | $AD_{SET\_1}$ | $Q_{SYS\_1,1}$ | $Q_{SYS\_1,2}$ | ... $Q_{SYS\_1,N}$ |
| | $AD_{SET\_2}$ | $Q_{SYS\_2,1}$ | $Q_{SYS\_2,2}$ | ... ... |
| | ... | ... | ... | ... ... |
| | $AD_{SET\_M}$ | $Q_{SYS\_M,1}$ | $Q_{SYS\_M,2}$ | ... $Q_{SYS\_M,N}$ |

The result is an N×M matrix provided in Table 1. N is the number of Natural System Qs ($Q_{NAT}$) tested during calibration. The number of $Q_{NAT}$ values that will be encountered in practice is virtually infinite, however, if the calibration dataset covers the full range of possible $Q_{NAT}$ values with enough granularity, any $Q_{NAT}$ value found in practice can be approximated using the nearest value in the calibration table. M is the number of possible settings implemented in the variable active damping circuit. This is circuit dependent and can be scaled up easily.

The second dataset, provided in Table 2, relates the system Q to the most critical performance metrics for the tool: ringing and noise to signal ratio. These are measured over the expected range of echo spacing levels, which can be segregated into high and low to reduce the dimensions of the calibration database.

TABLE 2

| | | System Q | | |
|---|---|---|---|---|
| | | $Q_{SYS\_1,X}$ | $Q_{SYS\_2,X}$ | ... $Q_{SYS\_M,X}$ |
| Ringing With Respect to System Q and Echo Spacing for $Q_{NAT\_X}$ | | | | |
| Echo Spacing | $TE_{HIGH}$ | $RING_{HIGH,1,X}$ | $RING_{HIGH,2,X}$ | ... $RING_{HIGH,M,X}$ |
| | $TE_{LOW}$ | $RING_{LOW,1,X}$ | ... | ... $RING_{LOW,M,X}$ |
| NSR With Respect to System Q and Echo Spacing for $Q_{NAT\_X}$ | | | | |
| Echo Spacing | $TE_{HIGH}$ | $NSR_{HIGH,1,X}$ | $NSR_{HIGH,2,X}$ | ... $NSR_{HIGH,M,X}$ |
| | $TE_{LOW}$ | $NSR_{LOW,1,X}$ | ... | ... $NSR_{LOW,M,X}$ |

With this data, it is possible to find the optimal system Q level for a given logging condition. The optimal Q (and the optimal active damper setting) is that which minimizes the function below.

$$J(TE) = C_{NSR}(TE)\frac{NSR(TE)}{NSR_{NOMINAL}} + C_{RING}(TE)\frac{RING(TE)}{RING_{NOMINAL}} \quad \text{Equation 1}$$

The $NSR_{NOMINAL}$ and $RING_{NOMINAL}$ constants are used to normalize the performance metrics. The weights $C_{NSR}$ and $C_{RING}$ depend on the echo spacing of the segment to be executed. They can be defined as shown below in Table 3 to reflect that ringing is more important at low TE, and noise to signal ratio is more important at high TE. These can be re-adjusted as needed, but are expected to remain unchanged once the best set is found.

TABLE 3

| Echo Spacing (TE) | $C_{NSR}$ | $C_{RING}$ |
|---|---|---|
| HIGH | 0.9 | 0.1 |
| LOW | 0.1 | 0.9 |

The calibration datasets can be approximated using smooth mathematical functions and curve fitting, if needed. The resulting parametric equations can improve computational efficiency and simplify the optimization effort, but so far this has been unnecessary due to the size of the matrices at play. As illustrated, the data in Table 3 may be used in FIG. 8 at 816.

The effects of variable active damping on the tool's final output may also be eliminated. This can be done using a variable calibration parameter, which depends on the operating condition and the active damping setting. The data needed to calculate this parameter is already available from the data gathered to fill the tables in the previous section. The calibration data is tabulated as shown below in Table 4.

TABLE 4

Master-Calibration Parameter With Respect to Logging Conditions and Variable Active Damping Setting

| | | Natural System Q | | |
|---|---|---|---|---|
| | | $Q_{NAT\_1}$ | $Q_{NAT\_2}$ | ... $Q_{NAT\_N}$ |
| Variable Active Damping Setting | $AD_{SET\_1}$ | $CAL_{1,1}$ | $CAL_{1,2}$ | ... $CAL_{1,N}$ |
| | $AD_{SET\_2}$ | $CAL_{2,1}$ | $CAL_{2,2}$ | ... ... |
| | ... | ... | ... | ... ... |
| | $AD_{SET\_M}$ | $CAL_{M,1}$ | $CAL_{M,2}$ | ... $CAL_{M,N}$ |

Table 4 is indexed using the variable active damping setting from the digital control algorithm and the natural damping data from the calibration algorithm. The corresponding calibration parameter is used to "normalize" the measurement prior to reporting it to higher level data processing processes. This master calibration parameter may be used, for example, in 826 and 824, as necessary, according to FIG. 8.

Pre-processing and optimization of the calibration data can be completed off-line to obtain a direct mapping from $Q_{NAT\_X}$ to $AD_{SET\_Y}$ and $CAL_{Y,X}$. In this case, the optimal configuration and its corresponding calibration parameter become known as soon as $Q_{NAT\_X}$ is estimated, bypassing the need for real-time optimization. This can greatly simplify the software implementation.

Referring to FIG. 8, a method 800 for calibration of a nuclear magnetic resonance tool using variable damping control for a nuclear magnetic resonance data acquisition system is illustrated. At 802, a nuclear magnetic resonance sequence is started to activate a geological formation. At 804, active damping is disabled. At 806, auxiliary calibration data is collected. At 808, system Q is estimated. At 810, an optimal active damping setting is determined. At 812, optimal active damping setting is deployed for the system. Nuclear magnetic resonance data is then collected at 814. Nuclear magnetic resonance data is then calibrated at 816. At 818, if the nuclear magnetic resonance sequence is not completed, then the next nuclear magnetic resonance segment is proceeded to, where segment information is gathered and the process continues from 810. If the nuclear magnetic resonance sequence is completed as determined at 818, then the process returns to step 810 by going to the next segment 820 by gathering NMR segment information 821.

At step 810, multi-dimensional master calibration may be accomplished, as necessary in 826. After multi-dimensional master calibration is completed, the method may return to determine optimal active damping settings 810. After the estimation of the natural Q for the system 808, multi-dimensional master calibration 824 may also be accomplished. Similarly, multi-dimensional master calibration 824 may be performed after determination of optimal active damping setting 810.

Certain embodiments and features may have been described using a set of numerical upper limits and a set of numerical lower limits. It should be appreciated that ranges including the combination of any two values, e.g., the combination of any lower value with any upper value, the combination of any two lower values, or the combination of any two upper values are contemplated. Certain lower limits, upper limits and ranges may appear in one or more claims below. Numerical values are "about" or "approximately" the indicated value, and take into account experimental error, tolerances in manufacturing or operational processes, and other variations that would be expected by a person having ordinary skill in the art.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include other possible embodiments along with the full scope of equivalents to which such claims are entitled. Accordingly, the claims are not limited by the disclosure.

What is claimed is:

1. A method to calibrate a nuclear magnetic resonance tool, comprising:
   starting a nuclear magnetic resonance sequence from the nuclear magnetic resonance tool;
   disabling an active damping circuit in the nuclear magnetic resonance tool;
   collecting auxiliary calibration data for the nuclear magnetic resonance tool;
   estimating a natural Q value for the nuclear magnetic resonance tool;
   determining an optimal active damping setting for the tool;
   deploying the optimal active damping setting for the tool;
   collecting nuclear magnetic resonance response data generated from the nuclear magnetic resonance sequence; and
   calibrating the nuclear magnetic resonance data.

2. The method according to claim 1, further comprising:
   determining when the nuclear magnetic sequence is completed.

3. The method according to claim 2, wherein when the nuclear magnetic resonance sequence is not completed, a next nuclear magnetic resonance segment is gathered.

4. The method according to claim 2, wherein when the nuclear magnetic sequence is completed, the method returns to the determining the optimal active damping setting.

5. The method according to claim 2, further comprising:
   performing a multi-dimensional master calibration after the determining the optimal active damping setting.

6. The method according to claim 5, wherein after the performing the multi-dimensional master calibration after the determining the optimal active damping setting, the nuclear magnetic data are calibrated.

7. A method for processing nuclear magnetic resonance data, comprising:
   placing a nuclear magnetic resonance tool in a wellbore;
   starting a nuclear magnetic resonance sequence from the nuclear magnetic resonance tool;
   disabling an active damping circuit in the nuclear magnetic resonance tool;
   collecting auxiliary calibration data for the nuclear magnetic resonance tool;
   estimating a natural Q value for the nuclear magnetic resonance tool;
   determining an optimal active damping setting for the tool;
   performing a multi-dimensional master calibration master calibration based on the natural system Q and a variable active damping setting;
   deploying the optimal active damping setting for the tool;
   collecting nuclear magnetic resonance response data generated from the nuclear magnetic resonance sequence; and
   calibrating the nuclear magnetic resonance data based upon the Q value.

8. The method according to claim 7, further comprising:
   determining when the nuclear magnetic resonance sequence is completed.

9. The method according to claim 8, wherein when the nuclear magnetic resonance sequence is not completed, a next nuclear magnetic resonance segment is gathered.

10. The method according to claim 8, wherein when the nuclear magnetic resonance sequence is completed, the method returns to the determining the optimal active damping setting for the tool.

11. The method according to claim 8, further comprising:
performing a multi-dimensional master calibration after the determining the optimal active damping setting for the tool.

12. The method according to claim 11, wherein after the performing the multi-dimensional master calibration after the determining the optimal active damping setting, the nuclear magnetic data are calibrated.

\* \* \* \* \*